United States Patent [19]

Keller

[11] Patent Number: 5,318,441
[45] Date of Patent: Jun. 7, 1994

[54] METHOD OF CEPHALOMETRIC EVALUATION OF DENTAL RADIOGRAPHS

[76] Inventor: Duane C. Keller, 62 Grantwood, St. Louis, Mo. 63123

[21] Appl. No.: 945,869

[22] Filed: Sep. 17, 1992

[51] Int. Cl.⁵ ............................................. A61C 3/00
[52] U.S. Cl. ....................................... 433/68; 433/24; 433/72; 364/413.13
[58] Field of Search ................... 433/68, 24, 72, 215; 364/413, 414, 415; 128/777, 749; 378/162, 163, 164, 205

[56] References Cited

U.S. PATENT DOCUMENTS

| | | | |
|---|---|---|---|
| 4,528,627 | 7/1985 | Coben | 433/68 |
| 4,610,629 | 9/1986 | Schrems et al. | 433/72 |

*Primary Examiner*—John J. Wilson
*Attorney, Agent, or Firm*—Polster, Lieder, Woodruff & Lucchesi

[57] ABSTRACT

A method for cephalometric evaluation includes steps of generating radiographic, X-ray or other image of a patient's individual orthodontic structure, positioning this image in alignment with a graphical depiction of a norm value orthodontic structure, and comparing the individual's structure to the norm value structure to analyze development and to determine a course of orthodontic or other treatment.

8 Claims, 3 Drawing Sheets

METHOD OF CEPHALOMETRIC EVALUATION OF DENTAL RADIOGRAPHS

BACKGROUND OF THE INVENTION

This present invention relates to an improved method for cephalometric evaluation and more particularly to a method of analysis through comparison of depictions of structures in orthodontic patients to a normal value orthodontic and/or cranial structure for like patients of similar age or development.

The standard method for cephalometric evaluation of orthodontic patients is to take a radiograph (X-ray) and to plot specific points of interest. By plotting lines, angles and linear measurements, the practitioner is able to evaluate growth and development of an individual patient's orthodontic structures. These lines, angles and linear measurements are compared to other average or "norm" values of lines, angles and linear measurements as a base standard. The practitioner is required to carefully and, as accurately as possible, to plot out each point line and angle and measure each of these individually. Almost all methods of cephalometric analysis use the same specific points of interest for measurement. The practitioner focuses on points which yield the most helpful and consistent results for determining relative growth and development in orthodontic structures.

The measurements obtained from cephalometric analysis allow the practitioner to compare individual patients to average or norm patients of similar ages and ethnic backgrounds. One function of cephalometric analysis is to allow the practitioner to compare dental relations of a patient to individuals who exhibit normative occlusion. Another function is to compare skeletal relations of a patient's skeletal anteroposterior components to skeletal norms of similar individuals. The measurements also enable the practitioner to relate soft tissue outlines of a patient's face to ethnically similar individuals with normative occlusion. All of these functions enable the practitioner to establish the direction of growth and development in an individual's orthodontic structures. Once the direction of growth and development is established the practitioner can determine whether any orthodontic procedures are necessary to obtain a "normal" relationship. In addition, the measurements are helpful in determining whether an individual patient is at risk for certain types of temporomandibular joint (TMJ)dysfunction and if the patient already has TMJ dysfunction, the measurements help determine the desired steps for treatment.

Although the standard method of cephalometric analysis yields the desired results, there are several disadvantages which practitioners have struggled with for years. Manually plotting the specific points of interest and measuring the resulting lines and angles is extremely tedious and time consuming. The ability to obtain optimal precision is limited by the potential for human error in obtaining the measurements. The standard method is also subject to obvious radiographic distortion in areas where two overlapping structures are superimposed.

Various other features of the present invention will become obvious to one skilled in the art upon reading the disclosure set forth herein.

SUMMARY OF THE INVENTION

One of the objects of the present invention is to provide a method of cephalometric analysis that eliminates the need for plotting and measuring specific points, lines and angles.

Another object is to provide such a method which increases the accuracy of cephalometric analysis by decreasing the possibility of errors due to drafting mistakes or other mistakes likely to occur using the standard method of analysis.

Another object is to provide such a method which is quicker, easier and more cost effective than the standard method.

Another object is to provide such a method which allows the practitioner to compare an individual patient's orthodontic structures to a two dimensional norm orthodontic structure.

Another object is to provide such a method which allows the practitioner to compare orthodontic structures by region instead of being limited to specific points of interest.

Another object is to provide such a method which allows the practitioner to compare each region independently or to another selected region, or to a base (skull) reference.

Another object is to provide such a method which clearly depicts where the structures would be and where they actually are in relation to norm orthodontic structures.

Other objects of this invention will be apparent to those skilled in the art in light of the following descriptions and accompanying drawings.

In accordance with this invention, generally stated, an image of a patient's individual orthodontic structure is generated, as by taking a radiograph (X-ray). Using an image saves time and money compared to using linear measurements. The image is also not subject to potential drafting mistakes. In addition, the image provides a dramatic method for analysis since the practitioner is able to see an image of the structure itself instead of numbers representing the structure. The method further comprises positioning the individual orthodontic structure image in alignment with a graphical depiction (either a transparent depiction or a graphical display of such a picture on a computer display or the like) of an average or norm value orthodontic structure for a patient of similar age and ethnic background. And then a further step of comparing the image to the graphical depiction. This method of comparison is quicker and easier than the rigorous plotting and measuring involved in the standard method.

BRIEF DESCRIPTION OF THE DRAWINGS

Corresponding reference characters represent corresponding parts throughout the various drawing figures.

DESCRIPTION OF A PREFERRED EMBODIMENT

Figure 1:
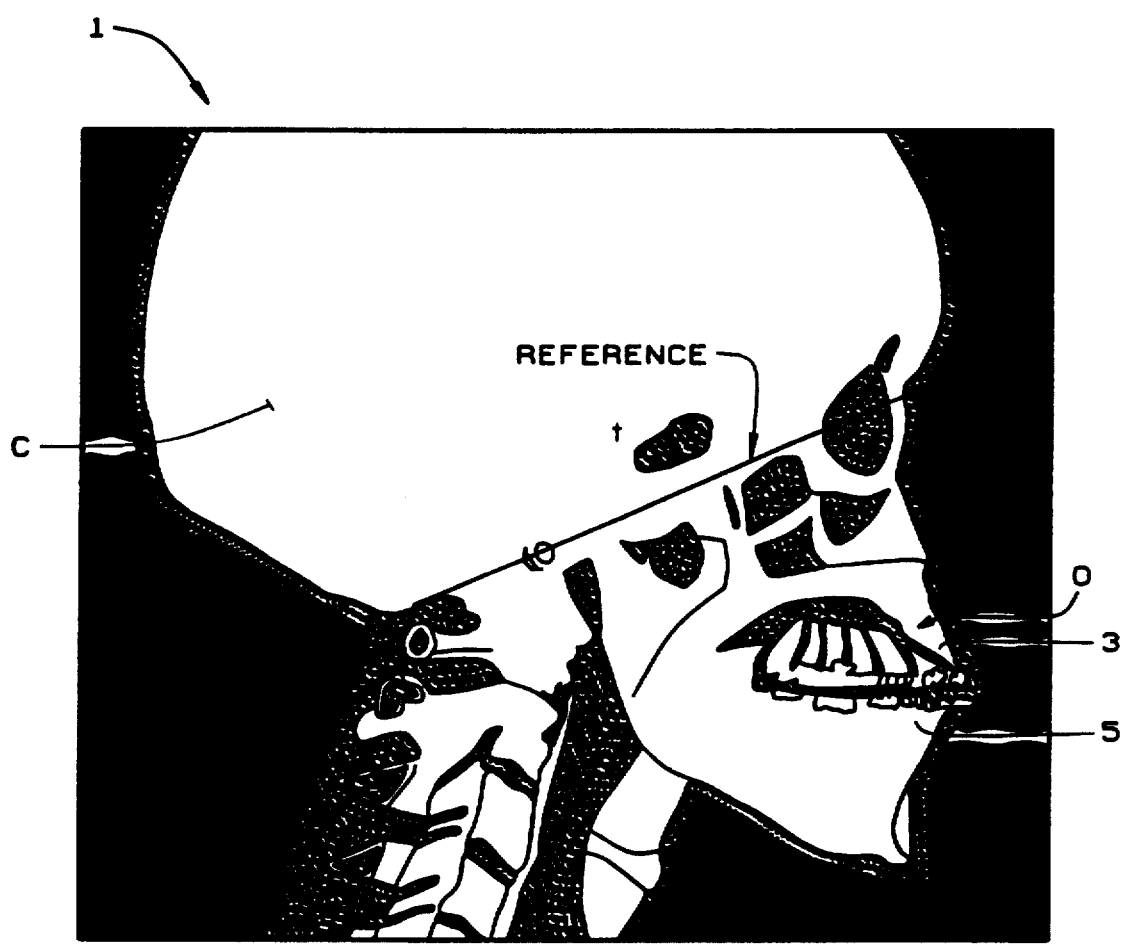
FIG. 1 is an image (a lateral radiograph), of a patient's orthodontic and cranial structure.

Referring now to the drawing figures, and more particularly to FIG. 1, a lateral radiographic (or X-ray) image, as generally indicated at 1, is shown for a particular patient. The radiographic or X-ray image is shown in side elevation and it depicts various structural features of the cranium C and of the patient's upper orthodontic structure 3 and the lower orthodontic structure 5. It will be understood that frontal images can be used with this method as well as lateral images.

In accordance with this method, the practitioner then establishes a reference line (or plane) R on the radiographic image 1 (as shown in FIG. 1). Reference line R is established by drawing a line on the radiographic image 1 from the bridge of the nasion to the lower base of the skull near the juncture of the mastoid process and the lowest portion occipital when viewed laterally. This line of reference extends through the eye socket and can, for example extend through the pterygomaxiallary fissure which is located interiorally of the zygomatic process.

Figure 2:
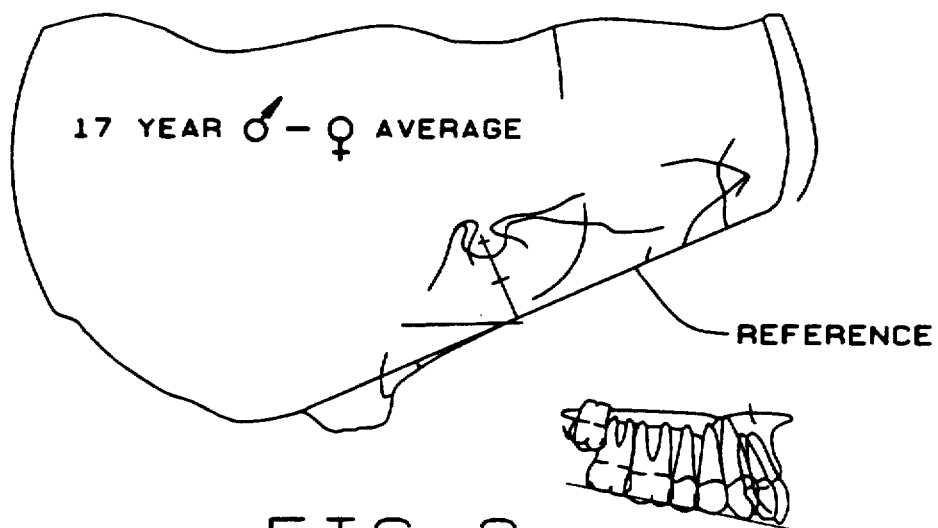
FIG. 2 is a graphical depiction, preferably on a transparent background or as displayed on a computer visual display, of a norm value orthodontic and/or cranial structure for a standard reference of similar race, age and/or degree of development showing a selected orthodontic structure (e.g., the upper teeth)
Figure 4:
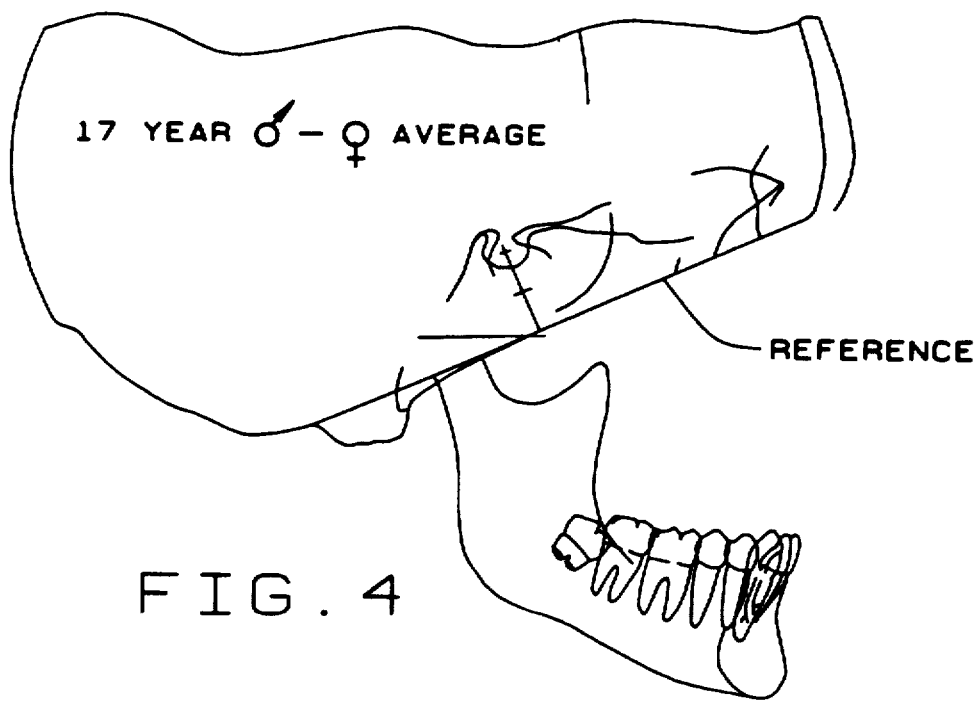
FIG. 4 is a view similar to FIG. 2 of a norm value orthodontic and/or cranial structure for a standard reference showing the lower teeth.

Further in accordance with this method of cephalometric analysis, the practitioner selects a graphical depiction, as shown in FIGS. 2 or 4, of an average or norm value orthodontic structure for a patient of similar age and ethnic background to serve as a reference. For example, if the actual patient who's radiograph is illustrated in FIG. 1 is an average 17 year old male or female, then the graphical depiction for an average 17 year old of similar and ethnic background would be selected. However, it has been found that in accordance with this method if the actual radiograph for a patient is compared to his or her norm value orthodontic structure of similar age and ethnic background and if there is a general state of underdevelopment, then the norm value structure of a different age reference is utilized. It is then assumed that all other cranial and orthodontic structure of the patient are in proportion to the reference.

Figure 5:
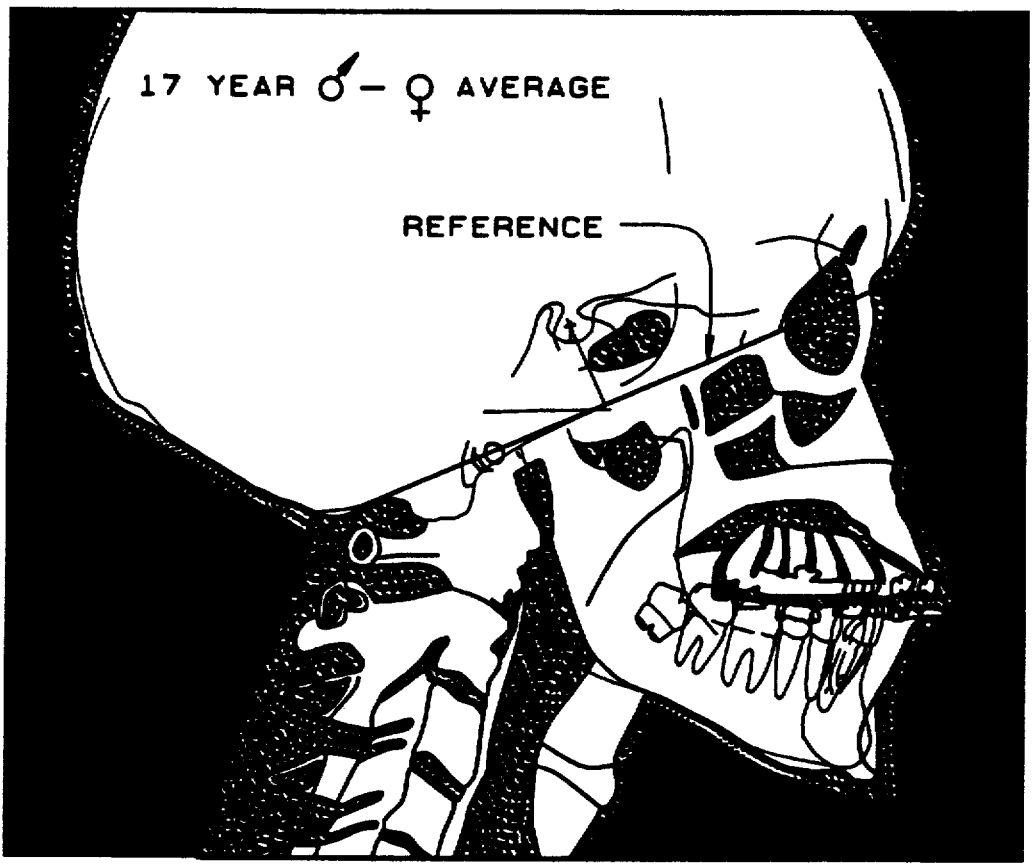
FIG. 5 is an overlay of the norm value orthodontic structure shown in FIG. 3 overlayed on the patient's image of FIG. 1 showing deviations of the patient's lower teeth orthodontic structure to that of the norm value.

Further in accordance with the method of this invention, the selected norm value orthodontic structure, as shown in FIGS. 2 or 4, are on a transparent background which may be laid over the radiograph image shown in FIG. 1. The reference line R established on the radiograph is brought into register with a similar reference line or plane on the norm value orthodontic structure to form the overlay graphical depiction, as shown in FIGS. 3 or 5.

Figure 3:
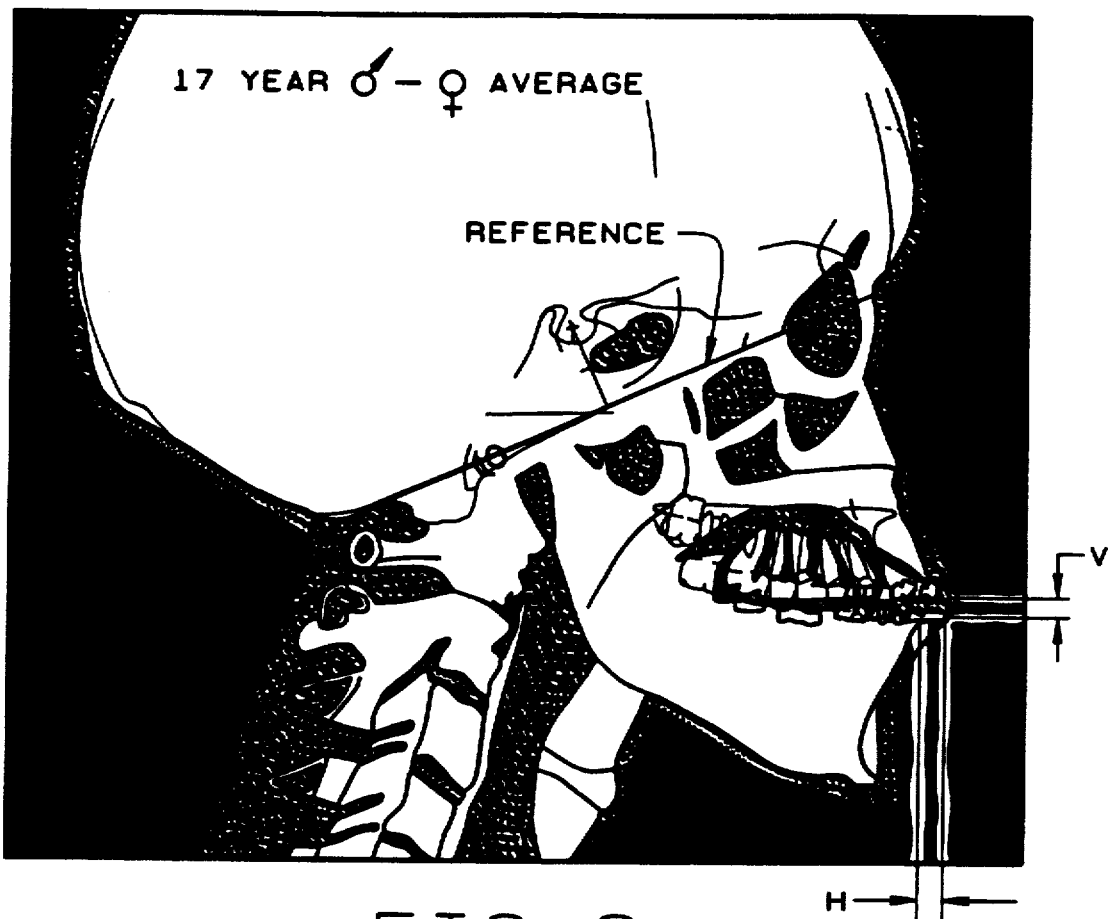
FIG. 3 shows the graphical depiction of the norm value orthodontics structure for the cranium and upper teeth of FIG. 2 overlayed on the patient's radiograph of FIG. 1 thus graphically showing deviations of the patient's upper teeth orthodontic structure (as shown on the radiographic image) to that of the norm value reference shown in FIG. 2.

More specifically, the overlaid image shown in FIG. 3 shows a transparency with the norm value orthodontic structure of FIG. 2 properly positioned on the radiographic image 1 with the reference lines R on the image and on the reference on the norm value orthodontic depiction being in register with one another. The resulting overlay image shown in FIG. 3 then illustrates the relationship of, for example, the upper teeth reference (on the norm value orthodontic structure) as shown in FIG. 2 in relation to the corresponding patient's upper teeth as shown in FIG. 1.

As shown in FIG. 3, the overlay illustrates vertical and horizontal deviations V and H of the patient's upper teeth relative to the upper teeth of the norm value orthodontic reference structure shown on the transparent overlay (FIG. 2). This readily shows the practitioner where the patient's orthodontic structures are in relation to norm orthodontic structures and also illustrates the amount of orthodontic correction required. It will be further appreciated that this method allows the practitioner to compare orthodontic structures by a particular region (e.g., the patient's upper teeth) instead of being limited to specific points of interest as were common in prior cephalometric analysis methods.

In a like manner, the norm value orthodontic structure for the patient's lower jaw, as is illustrated in FIG. 4 may be overlaid with the patient's radiograph of FIG. 1 so as to illustrate the position of the patient's lower teeth with respect to the norm value of the lower teeth of such orthodontic structure for a patient of similar ethnic background. Again, deviation of the patient's lower teeth to the norm value position and location of a known standard may be determined as was in the case of FIG. 3 so as to determine the direction and the amount of orthodontic correction required.

Figure 6:
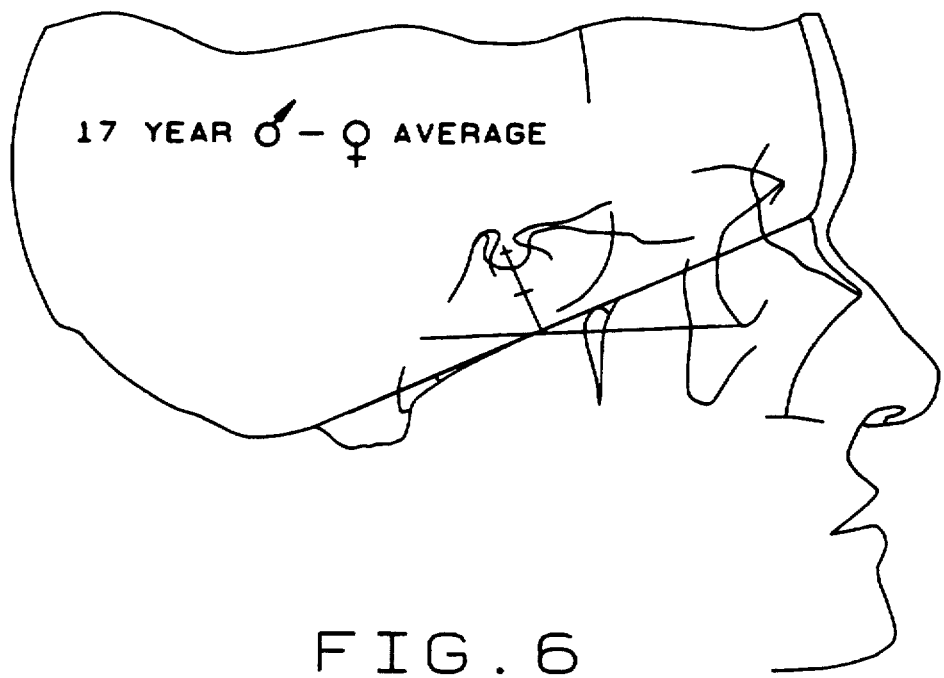
FIG. 6 is a norm value reference of the soft tissue structure including the nose and lips and other soft tissue structure which may be overlayed with FIG. 1 (not shown) to graphically show the normal value location of such soft tissue to the actual location of the patient's soft tissue.

FIG. 6 illustrates a norm value reference for the facial soft tissue features of the patient in relation to the cranial and orthodontic structures illustrated in the norm value overlays shown in FIGS. 2 and 4. It will be appreciated that following a course of orthodontic treatment that, within a limited degree, the position of the patient's lips and chin may be modified to obtain a desired result.

In use, the method of the present invention involves first generating an image, preferably a radiographic image as shown in FIG. 1 of an individual's orthodontic structures, including the upper and lower teeth. Then, in the manner explained above, a norm value standard orthodontic structure is selected for the patient having a similar age and ethnic background, or being of a similar stage of development. Then, the individual orthodontic structural image is shown on the radiograph of FIG. 1 is positioned in alignment with the graphical depiction of the norm value orthodontic structure as shown on the transparency of FIG. 2 or 4. Then, the individual patient's orthodontic structural image, has shown on the radiograph of FIG. 1 may be compared to the norm value orthodontic structure of FIGS. 2 or 4 whereby the practitioner may evaluate development of the individual orthodontic structures and determine the course of treatment, the amount and direction of orthodontic treatment required.

The above method using the transparent overlay references of FIGS. 2 and 4 is preferred. However, it will be appreciated that the patient's radiographic image may be graphically displayed on a computer screen and the overlay reference may be combined with the patient's image on the computer screen rather than physically overlaying a transparent reference over the patient's X-ray.

It will be understood that over an extended course of orthodontic treatment, other radiographic images similar to FIG. 1 may be taken and compared to the norm value orthodontic structure so as to monitor the treatment and to make adjustments to the orthodontic structure.

Inasmuch as numerous changes or modifications may be made to the preferred embodiment of the invention as described in detail hereinabove without departing from the spirit and scope of the invention, it is therefore specifically noted that the scope of the invention is to be determined solely by the language of the following claims.

I claim:

1. Method of evaluating the relationship of individual orthodontic structures for a patient using a graphical depiction of a norm value orthodontic structure for said patient, said method comprising the steps of:
   a. generating a radiographic image of said individual orthodontic structures for said patient;
   b. positioning said individual orthodontic structure radiographic image in alignment with said graphical depiction of said norm value orthodontic structures for said patient; and
   c. graphically comparing said individual orthodontic structure radiographic image with said graphical depiction of said norm value orthodontic structure to evaluate development of said individual orthodontic structures.

2. A method of claim 1 further comprising selecting said norm value orthodontic structure by determining a cranial base reference for said patient.

3. The method of claim 2 wherein said step of selecting said norm value orthodontic structure comprises the nasion, the base of the skull, and pterygomaxillary fissure, or other selected reference points.

4. The method of claim 1 wherein said step of generating said image of said individual orthodontic structure comprises taking a radiographic image of the midface and upper teeth.

5. The method of claim 1 wherein said step of generating said image of said individual orthodontic structure comprises taking a radiographic image of the midface and upper teeth together with the sinuses, teeth, and related structures.

6. The method of claim 1 wherein said step of generating said image of said individual orthodontic structure comprises taking a radiographic image of the lower jaw and lower teeth.

7. The method of claims 4, 5, or 6 wherein said step of generating said image of said individual orthodontic structure further comprises taking a radiographic image of the surrounding soft tissue structure of the patient including the nose, lips, chin or other related soft tissue structure.

8. The method of claim 1 further comprising repeating the steps of claim 1 periodically throughout a course of treatment for the patient, monitoring the growth and development of said individual orthodontic structures of said patient over time, and graphically comparing the actual growth of said individual orthodontic structures to said image of said norm value orthodontic structure with said image serving as a reference.

* * * * *